US007568579B2

(12) United States Patent
Moore

(10) Patent No.: US 7,568,579 B2
(45) Date of Patent: Aug. 4, 2009

(54) HIGH STABILITY PACKAGE FOR DENTAL TREATMENT DEVICES

(75) Inventor: Scott Eric Moore, Bountiful, UT (US)

(73) Assignee: Ultradent Products, Inc., South Jordan, UT (US)

(*) Notice: Subject to any disclaimer, the term of this patent is extended or adjusted under 35 U.S.C. 154(b) by 668 days.

(21) Appl. No.: 11/284,472

(22) Filed: Nov. 22, 2005

(65) Prior Publication Data
US 2007/0114139 A1 May 24, 2007

(51) Int. Cl.
B65D 73/00 (2006.01)

(52) U.S. Cl. .................. 206/368; 206/63.5; 206/467

(58) Field of Classification Search ............ 206/63.5, 206/368, 369, 484, 461, 467, 469, 470, 471
See application file for complete search history.

(56) References Cited

U.S. PATENT DOCUMENTS

| 3,488,252 | A | | 1/1970 | Lamar |
| 4,816,093 | A | | 3/1989 | Robbins, III ................. 156/69 |
| 4,867,680 | A | * | 9/1989 | Hare et al. ................... 433/37 |
| 4,927,690 | A | | 5/1990 | Welsh ........................ 428/35.7 |
| 5,085,927 | A | | 2/1992 | Dohrer ........................ 428/220 |
| 5,135,392 | A | * | 8/1992 | Polansky ..................... 433/37 |
| 5,240,415 | A | * | 8/1993 | Haynie ........................ 433/216 |
| 5,310,587 | A | | 5/1994 | Akahori et al. ............. 428/35.2 |
| 5,323,787 | A | * | 6/1994 | Pratt ........................... 128/862 |
| 5,346,061 | A | * | 9/1994 | Newman et al. ............ 206/221 |
| 5,415,544 | A | * | 5/1995 | Oxman et al. ................. 433/48 |
| 5,460,527 | A | * | 10/1995 | Kittelsen ..................... 433/215 |
| 5,658,625 | A | | 8/1997 | Bradfute et al. ............ 428/34.9 |
| 5,741,566 | A | | 4/1998 | Högström et al. .......... 428/35.2 |
| 5,772,432 | A | * | 6/1998 | Jordan et al. .................. 433/37 |
| 5,863,202 | A | | 1/1999 | Fontenot et al. |
| 5,912,070 | A | | 6/1999 | Miharu et al. .............. 428/214 |
| 5,947,278 | A | * | 9/1999 | Sawhney et al. ............ 206/216 |
| 5,972,445 | A | | 10/1999 | Kimura et al. ............. 428/35.4 |

(Continued)

FOREIGN PATENT DOCUMENTS

JP 5178365 7/1993

(Continued)

OTHER PUBLICATIONS

Tekni-Plex Introduces First Blister Pack Films Combining Topas® COC and PCTFE Moisture Barriers, Celanese Chemicals—News URL: http://www.celanese.com/index/mr_index/mr_news/c_news_fullpage-link?id=22039 (Jun. 1, 2005).

(Continued)

Primary Examiner—Jacob K Ackun, Jr.
(74) Attorney, Agent, or Firm—Workman Nydegger

(57) ABSTRACT

A pre-packaged dental treatment system including a dental treatment device having a barrier layer configured for placement over at least a portion of a person's teeth, a dental treatment composition (e.g., a bleaching composition) disposed adjacent to the barrier layer, and a sealed packaging container within which the dental treatment device is disposed. At least a portion of the packaging container includes a laminated polymer material that is substantially impervious to water molecules, which prevents the dental treatment composition from drying out. The laminated polymer material is optionally also a barrier to oxygen molecules.

17 Claims, 7 Drawing Sheets

U.S. PATENT DOCUMENTS

| | | | |
|---|---|---|---|
| 5,993,949 A | 11/1999 | Rosenbaum et al. | 428/213 |
| 6,379,147 B1 * | 4/2002 | Georgakis et al. | 433/37 |
| 6,548,108 B1 | 4/2003 | Lohwasser et al. | |
| 6,719,995 B2 | 4/2004 | Rajaiah et al. | |
| 6,872,462 B2 | 3/2005 | Roberts et al. | |
| 2004/0104142 A1 | 6/2004 | Dobler et al. | 206/531 |
| 2004/0187882 A1 | 9/2004 | Vink et al. | 131/347 |
| 2004/0197567 A1 | 10/2004 | Tsai et al. | 428/421 |
| 2005/0061705 A1 | 3/2005 | Spallek et al. | 206/528 |
| 2005/0084636 A1 | 4/2005 | Papenfuss et al. | 428/35.7 |
| 2005/0186539 A1 | 8/2005 | McLean et al. | |
| 2005/0249903 A1 | 11/2005 | Kendig et al. | |

FOREIGN PATENT DOCUMENTS

| | | |
|---|---|---|
| JP | 11105217 | 4/1999 |
| JP | 11309822 | 11/1999 |

OTHER PUBLICATIONS

Trombley, K. et al., The Benefits of Cyclic Olefin Copolymer, *Medical Devicelink*, URL: http://www.devicelink.com/pmpn/archive/04/06/005.html (Jun. 2004).

Barrier films are an especially important option with environmental concerns, Coextruded Polymer, Coextrusion Film, Barrier Materials, *Jobwerx Manufacturing Network*, URL: http://www.jobwerx.com/news/celanese_tekni-plex_news-id_695_2.html (Jun. 1, 2005).

Blisterpackaging Materials for Pharmaceuticals, *Sepha Blisterpacking Solutions*, URL: http://www.sepha.com/materials.htm (Sep. 2004).

Plastic blisterfoil, transparent and thermoformable, Alcan Packaging, Polybar®-COC URL: http://www.alcanpackaging.com/about/PDF/Amparis_EN.pdf (Sep. 2003).

Innovative New Developments in High Barrier Pharmaceutical Packaging And Generic Pharmaceutical Packaging Solutions URL: http://bbriefings.com/pdf/15/pg031_t_klockne/pdf (Jun. 2005).

Forcinio, H., Blister News: COC Resin, Foil, and Lidding Innovations, *Pharmaceutical Technology* (Jun. 2001) URL: http://ptech.adv100.com/pharmtech/data/articlestandard/pharmtech/252002/22641/article.pdf.

* cited by examiner

HIGH STABILITY PACKAGE FOR DENTAL TREATMENT DEVICES

BACKGROUND OF THE INVENTION

1. The Field of the Invention

The present invention generally relates to the field of dental treatment materials. More particularly, the invention relates to packaging materials for dental treatment systems that can be used to bleach or otherwise treat a patient's teeth.

2. The Relevant Technology

Virtually all people desire white or whiter teeth. To achieve this goal, people have veneers placed over their teeth or have their teeth chemically bleached. A common bleaching method involves the use of a dental tray that is custom-fitted to a person's teeth and that is therefore comfortable to wear. One type of customized tray is made from a stone cast representative of a person's teeth. Another is customized directly using a person's teeth as a template (e.g., "boil-and-bite" trays).

Non-customized trays and strips that can be placed over a user's teeth have also been used. Non-customized trays are generally provided in multiple sizes that approximate the shapes and sizes of a variety of users' dental arches, while strips can be folded around the dental arch and under the occlusal tooth surfaces so as to cover at least a portion of the tooth surfaces of the dental arch.

A dental bleaching composition is often supplied in a separate container (e.g., a syringe or tube) from which it can be dispensed into the dental tray prior to placing the tray over the person's teeth. Alternatively, some dental bleaching trays and dental bleaching strips are provided pre-filled and/or pre-coated with a dental bleaching composition.

One disadvantage of pre-filled dental trays is that the dental bleaching compositions are typically sealed within packaging containers that are not completely impervious to water and oxygen molecules. A typical example of an existing package includes a foil or other peelable cover sealed over a rigid plastic support layer. Although the foil peelable cover may act as an effective barrier to water molecules, existing rigid plastic support layers are much less effective in preventing diffusion of water molecules therethrough over time. These existing packaging systems allow a small amount of water to be diffused across the plastic barrier, which can cause the bleaching compositions to eventually lose potency, particularly when stored at room temperature.

Typically water diffuses out of the dental treatment composition and across the plastic support layer of the packaging container, resulting in a dried out and ineffective treatment (e.g., bleaching) composition. Loss of water can decrease stability, resulting in decreased bleaching ability over time. In addition, diffusion of oxygen and water can also reduce stability since it is believed that peroxides release oxygen and water upon decomposition, and the ability of released oxygen and water to diffuse out of the package can shift the equilibrium toward increased peroxide decomposition.

Because of these disadvantages, it is recommended that many pre-filled bleaching systems be stored in a refrigerated environment prior to use. Refrigerated storage increases the stability of peroxide bleaching agents, thereby extending the shelf life of the packaged product. Such storage is often impractical, particularly for dental treatment systems intended for over-the-counter sale where refrigerated shelving may not be available practical.

It would be an improvement in the art to provide a pre-filled pre-packaged dental treatment system including a sealed packaging container that is substantially impervious to water molecules in order to thereby improve shelf life of the dental treatment composition (e.g., bleach).

SUMMARY OF THE INVENTION

The present invention is directed to a pre-packaged dental treatment system comprising (1) a dental treatment device including (a) a barrier layer configured for placement over at least a portion of a person's teeth and (b) a dental treatment composition disposed adjacent to the barrier layer, and (2) a sealed packaging container within which the dental treatment device is disposed. At least a portion of the packaging container includes a laminated polymer material that is substantially impervious to water molecules.

The dental treatment device may include a barrier layer of any suitable shape. In some examples, the barrier layer may be configured as a tray having a tray body comprising walls and a trough, while other examples may include a barrier layer configured as a thin strip that is initially substantially flat. During use, an initially flat strip is placed over at least a portion of the person's teeth, and then a portion of the strip may be folded over the occlusal surface of the person's teeth for the duration of treatment.

The dental treatment composition may include one or more of a dental bleaching agent, a desensitizing agent, a remineralizing agent, an antimicrobial agent, an anti-plaque agent, an anti-tartar agent, a gingival soothing agent, an anesthetic, an anti-oxidant, or a mouth freshening agent.

With regard to the packaging material, one laminated polymer material may include an inner layer formed of a cyclic olefin copolymer (COC) that acts as a substantially impervious barrier to water molecules. The laminate material also includes two outer layers (e.g., polypropylene and/or polyethylene) formed adjacent both sides of the inner layer of COC. In other words, the laminate material may comprise a core of a COC sandwiched between two outer layers (e.g., of polypropylene and/or polyethylene). The outer layers provide increased strength to the laminate material as COC by itself has poor structural strength. The laminated polymer material prevents water molecules from diffusing through the sealed packaging system, causing the treatment composition to dry out or otherwise lose potency. In addition, the laminate material also prevents water molecules outside the package from penetrating into the sealed container. Other water molecule barrier materials that may be used in addition to or instead of COC include a polychlorotrifluoroethylene (e.g., ACLAR). Additional materials that may be used as oxygen barrier materials include ethylvinyl hydroxide (EVOH) and/or a nitrile copolymer (e.g., BAREX).

In one embodiment, the laminated polymer material may be shaped and formed (e.g., through thermoforming) into a rigid support base, over which a foil cover may be adhered. Such a packaging container provides very good water molecule barrier characteristics, as both the foil cover and the laminated polymer material are substantially impervious to diffusion of water molecules. The cover may alternatively be formed of paper, a polymer, a laminate, or combinations thereof (e.g., a laminate including a paper or foil layer).

The packaging materials allow the treatment compositions to remain stable so as to have a shelf life of at least about 12 months, preferably at least about 18 months, and more preferably at least about 24 months, even when the systems are stored at room temperature. Some packaged systems may allow the treatment compositions to remain stable for as long as 48 months or more.

These and other benefits, advantages and features of the present invention will become more full apparent from the following description and appended claims, or may be learned by the practice of the invention as set forth hereinafter.

BRIEF DESCRIPTION OF THE DRAWINGS

In order that the manner in which the above recited and other benefits, advantages and features of the invention are obtained, a more particular description of the invention briefly described above will be rendered by reference to specific embodiments thereof which are illustrated in the appended drawings. Understanding that these drawings depict only typical embodiments of the invention and are not therefore to be considered limiting of its scope, the invention will be described and explained with additional specificity and detail through the use of the accompanying drawings in which.

DETAILED DESCRIPTION OF THE PREFERRED EMBODIMENTS

I. Introduction and Definitions

Figure 1A:
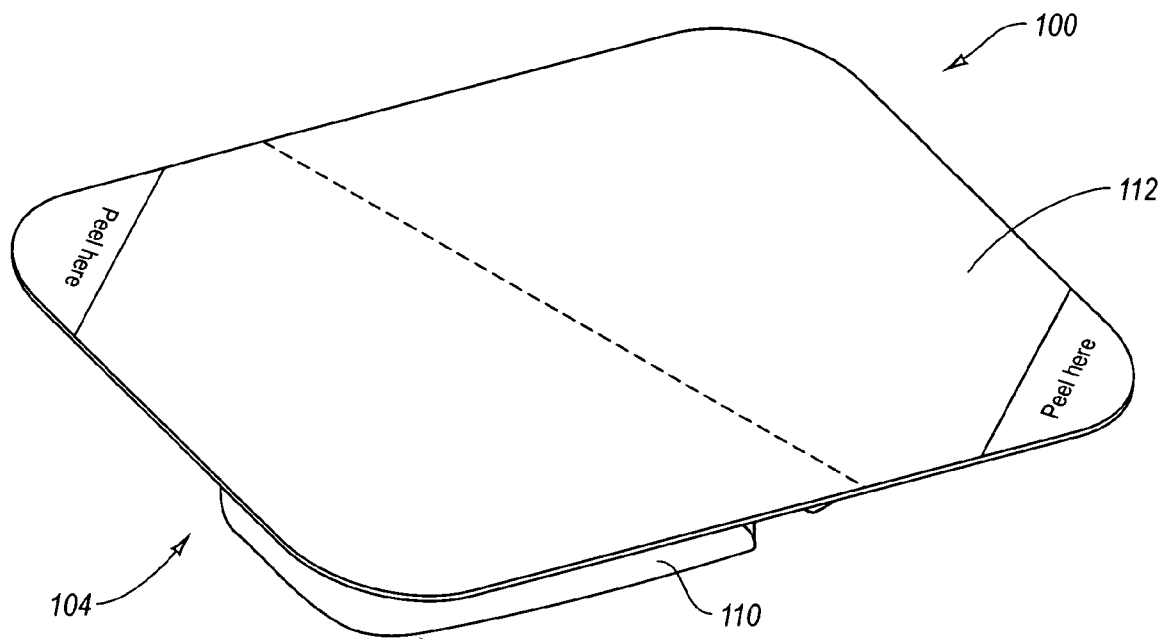
FIGS. 1A-1C illustrate various views of an exemplary pre-filled packaged dental treatment system according to the present invention.

A detailed description of the invention will now be provided with specific reference to figures illustrating preferred embodiments of the invention. It will be appreciated that like structures will be provided with like reference designations. Certain terms used throughout the detailed description will now be defined.

The term "barrier layer", as used herein, refers to one or more layers of a material that protects the dental treatment composition (e.g., a bleaching composition) from ambient moisture and saliva found within a person's mouth when the dental treatment device is placed over the person's teeth. The barrier layer may be configured as a strip that is initially substantially flat, or it may be shaped (e.g., as a dental tray).

The term "viscous gel" or "gel", as used herein, shall refer to dental treatment compositions that have been formulated or processed so that they do not readily flow by the force of gravity but are viscous so that they can be expressed from a syringe orifice or other dispensing means known in the art.

At some point, when the viscosity of a highly viscous gel becomes so great as to yield a composition that is substantially solid but still plastically deformable, it may be considered to be a "stiff putty". The difference between a "viscous gel" and a "stiff putty" is matter of degree. Likewise, a "stiff putty" can become so stiff or rigid as to become a "solid".

The term "substantially solid", as used herein, refers to a dental treatment composition that is in a solid or semi-solid condition. In one aspect, a "substantially solid" composition can be characterized as a cohesive mass that does not readily flow or separate when subjected to gravitational forces and which cannot be readily expressed through a syringe outlet or other similarly-sized opening or orifice. Thus, the term "substantially solid" excludes runny liquids, viscous liquids, and even thick gels that are able to flow when subjected to gravity and/or which can be readily expressed through a syringe outlet or other similarly-sized opening or orifice. The term "substantially solid", when used in the context of a dental treatment composition, also excludes dry particulate compositions or powders because dry particulates and powders readily flow when subjected to gravity and/or are readily separated (i.e., the particles as a whole have little or no internal cohesion). Moreover, powders or particulates, when viewed as a whole, are not coherent or solid.

The term "molecular weight", as used herein, shall refer to number average molecular weight expressed in Daltons, unless otherwise specified.

The present invention is directed to a pre-packaged dental treatment system including a dental treatment device having a barrier layer configured for placement over at least a portion of a person's teeth, a dental treatment composition disposed adjacent to the barrier layer, and a sealed packaging container within which the dental treatment device is disposed. At least a portion of the packaging container includes a laminated polymer material that is substantially impervious to water molecules.

II. Exemplary Pre-Packaged Dental Treatment Systems

Figure 1B:
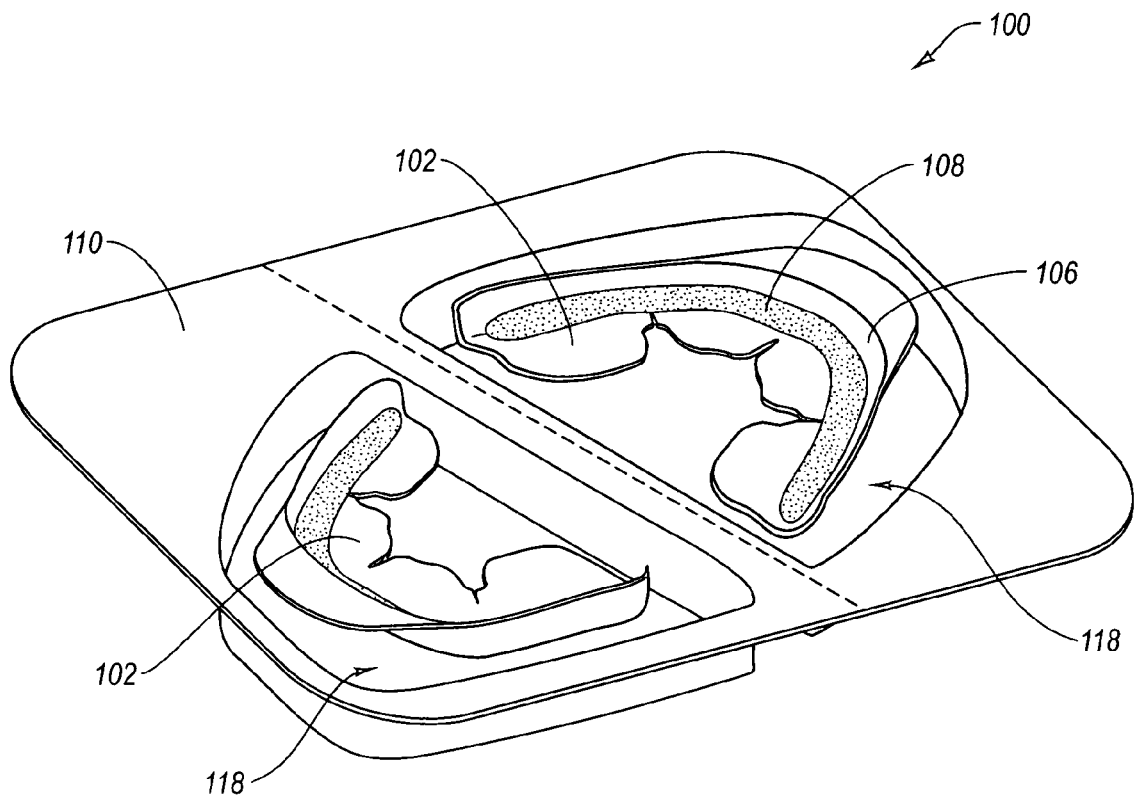
Figure 1C:
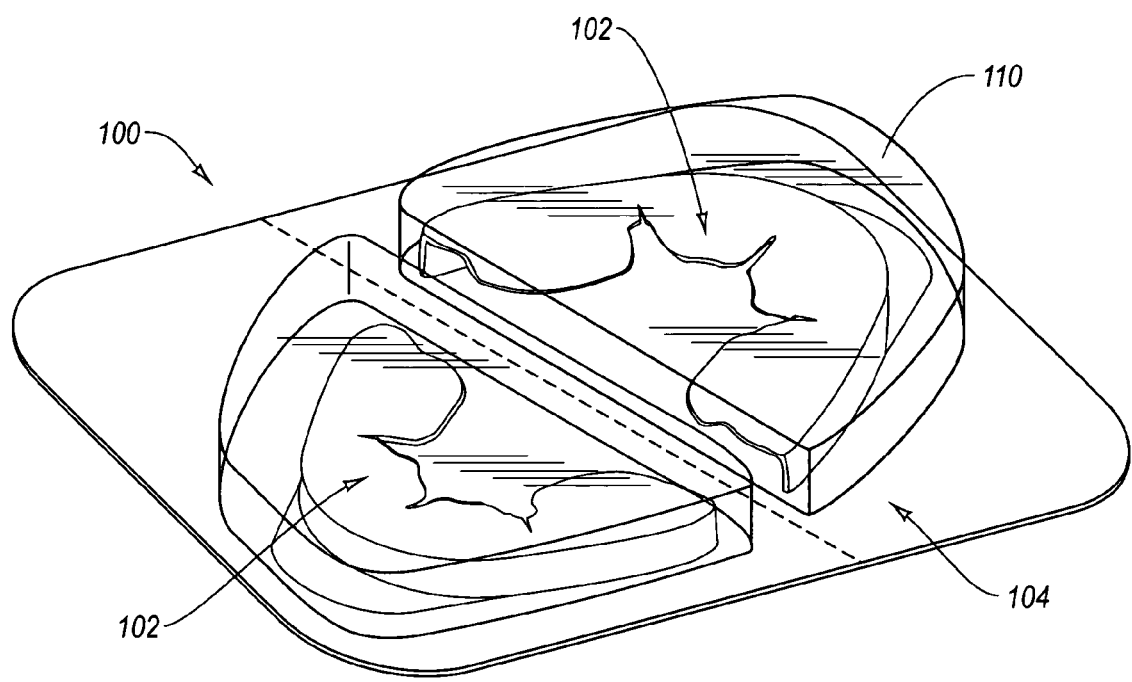

FIGS. 1A-1C illustrate an exemplary pre-packaged dental treatment system 100 that includes two dental treatment devices 102. FIG. 1A illustrates a top perspective view of a sealed packaging container 104 that includes an opaque foil cover 112 sealed over a rigid support layer 110. FIG. 1B illustrates the treatment system 100 with foil cover 112 removed, while FIG. 1C illustrates a bottom perspective view of treatment system 100 (i.e., system 100 has been turned over).

Treatment system 100 includes at least one dental treatment device 102 and at least one sealed packaging container 104. Although illustrated as including two dental treatment devices 102, system 100 may include more or fewer devices, as desired.

Dental treatment device 102, as illustrated, includes a barrier layer 106 and a dental treatment composition 108 disposed adjacent to the barrier layer 106. The dental treatment composition 108 may include any desired type of treatment agent. For example, the treatment agent may comprise one or more of a dental bleaching agent; a desensitizing agent (e.g., potassium nitrate, other potassium salts, citric acid, citrates, or sodium fluoride); a remineralizing agent (e.g., sodium fluoride, stannous fluoride, sodium monofluorophosphate, or other fluoride salts); antimicrobial agents (e.g., chlorhexidine, triclosan, sodium benzoate, parabens, tetracycline, phenols, or cetyl pyridinium chloride); an anti-plaque agent; an anti-tartar agent (e.g., pyrophosphates); a gingival soothing agent (e.g., aloe vera, mild potassium nitrate, or isotonic solution-forming salts); an anesthetic (e.g., benzocaine, lidocaine, or the like); an anti-oxidant (e.g., vitamin A, vitamin C, vitamin E, other vitamins, or carotene); or a mouth freshening agent (e.g., camphor or wintergreen).

Examples of dental bleaching agents include, but are not limited to, one or more of aqueous hydrogen peroxide, carbamide peroxide, metal perborates (e.g., sodium perborate), metal percarbonates (e.g., sodium percarbonate), metal peroxides (e.g., calcium peroxide), metal chlorites or hypochlorites, peroxy acids (e.g., peroxyacetic acid), or peroxy acid salts.

The dental treatment composition 108 may also include a thickening agent. Examples of thickening agents include a wide variety of hydrophilic polymers. Examples of hydrophilic polymer thickening agents include, but are not limited to, polyvinyl pyrrolidone (PVP), PVP-vinyl acetate copolymers, carboxypolymethylene (e.g., CARBOPOL, sold by Novean, Inc.), polyethylene oxide (e.g., POLYOX, made by Union Carbide), polyacrylic acid polymers or copolymers (e.g., PEMULEN, sold by Novean, Inc.), polyacrylates, polyacrylamides, copolymers of polyacrylic acid and polyacrylamide, carboxymethylcellulose, carboxypropylcellulose, cellulosic ethers, polysaccharide gums, proteins, or the like.

Examples of dental bleaching compositions that may be used are disclosed in U.S. Pat. No. 6,860,736, titled ORAL TREATMENT DEVICES THAT INCLUDE A THIN, FLEXIBLE BARRIER LAYER AND AN ENDOSKELETON TREATMENT OR ADHESIVE COMPOSITION, hereby incorporated by reference.

The system includes means for sealing the dental treatment device so as to substantially prevent drying out and/or deactivation of the dental treatment composition. Sealing means may comprise a sealed packaging container in which the device is disposed. At least a portion of the container is formed of a laminate polymer material that is substantially impervious to water molecules and optionally oxygen molecules.

Container 104 is illustrated as including a rigid support layer 110 and a peelable cover 112. Peelable cover 112 has been removed in FIG. 1B in order to more clearly show the dental treatment devices 102 disposed within container 104. When it is desired to use the dental treatment device 102, the peelable cover 112 may be removed and the treatment device 102 is removed or separated from the support layer 110. At least a portion of container 104 is formed of a laminated polymer material that is substantially impervious to water molecules.

As illustrated, the rigid support layer 110 may be formed (e.g., by thermoforming) so as to include a well 118 for each dental treatment device 102. The wells 118 may be configured so as to allow for a headspace between the device 102 and the cover 112. When thermoforming the rigid support layer 110 from a polymer laminate sheet, the sheet may initially have a uniform thickness. During the thermoforming process, the area of the sheet that forms the well 118 may become significantly thinner (e.g., as little as 15% of original thickness) through the stretching and forming process. The initial thickness of the sheet is selected so as to be sufficient to allow the walls of the well 118 to still have sufficient thickness (e.g., preferably about 1 mil or more) so as to act as a substantially impervious barrier to water molecules. For example, in one embodiment, the initial thickness of the sheet (and the thickness of the rigid support layer 110 besides wells 118) is between about 6 and about 30 mils, preferably between about 12 and about 28 mils, and more preferably between about 15 and about 25 mils.

Preferably, the entire sealed packaging container 104 is formed of materials that are substantially impervious to water molecules. For example, peelable cover 112 may be formed of an opaque foil material, which acts as a very effective barrier to water molecules, while rigid support layer 110 is formed of a transparent laminated polymer material that is substantially impervious to water molecules, resulting in a complete packaging container that is able to effectively protect dental treatment composition 108 (e.g., a bleaching composition) within package 104.

Alternatively, both the peelable cover 112 and the support layer 110 may be formed of a laminated polymer material that is substantially impervious to water molecules. Although cover 112 is illustrated and described as being a foil peelable cover, alternative types of covers will be apparent to those skilled within the art (e.g., paper, polymer, laminate, or combinations thereof). In addition, the cover is not required to be peelable, but may simply be breakable or otherwise so as to allow a user to remove the dental treatment device from the package.

Figure 2A:
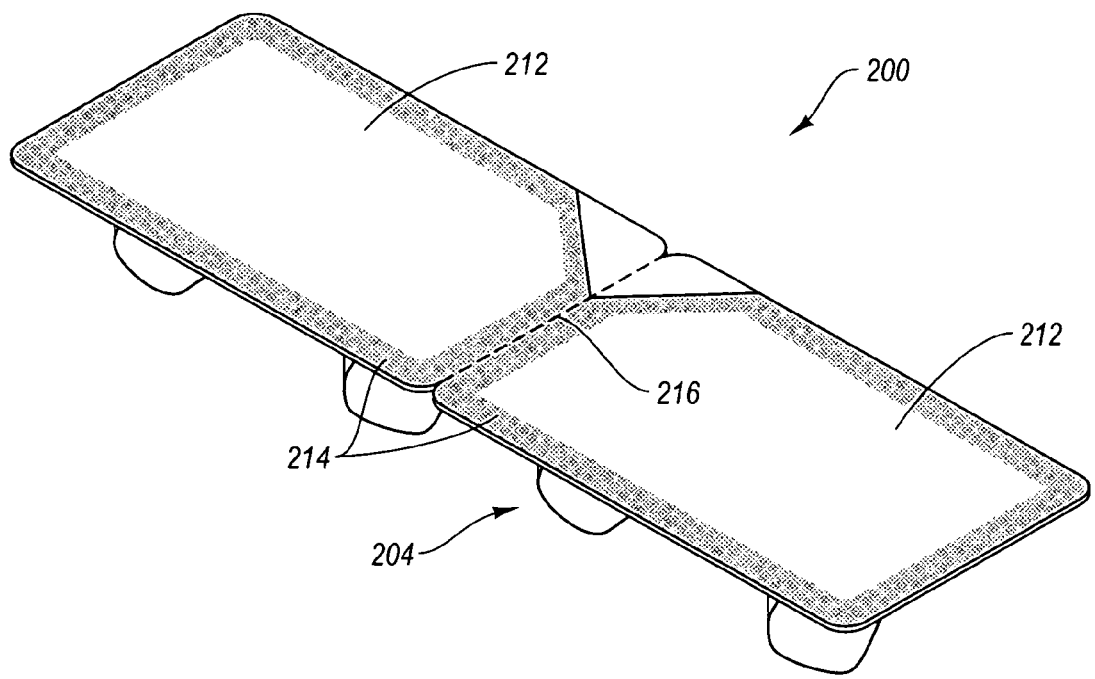
FIGS. 2A-2C illustrate various views of another exemplary pre-filled packaged dental treatment system.
Figure 2B:
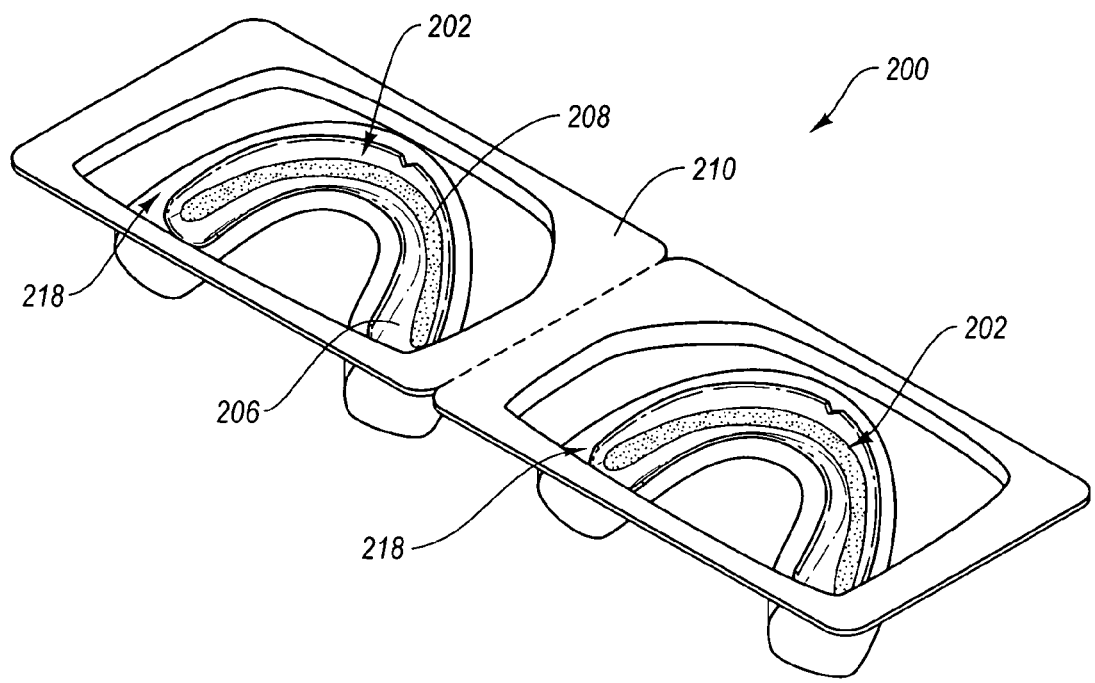
Figure 2C:
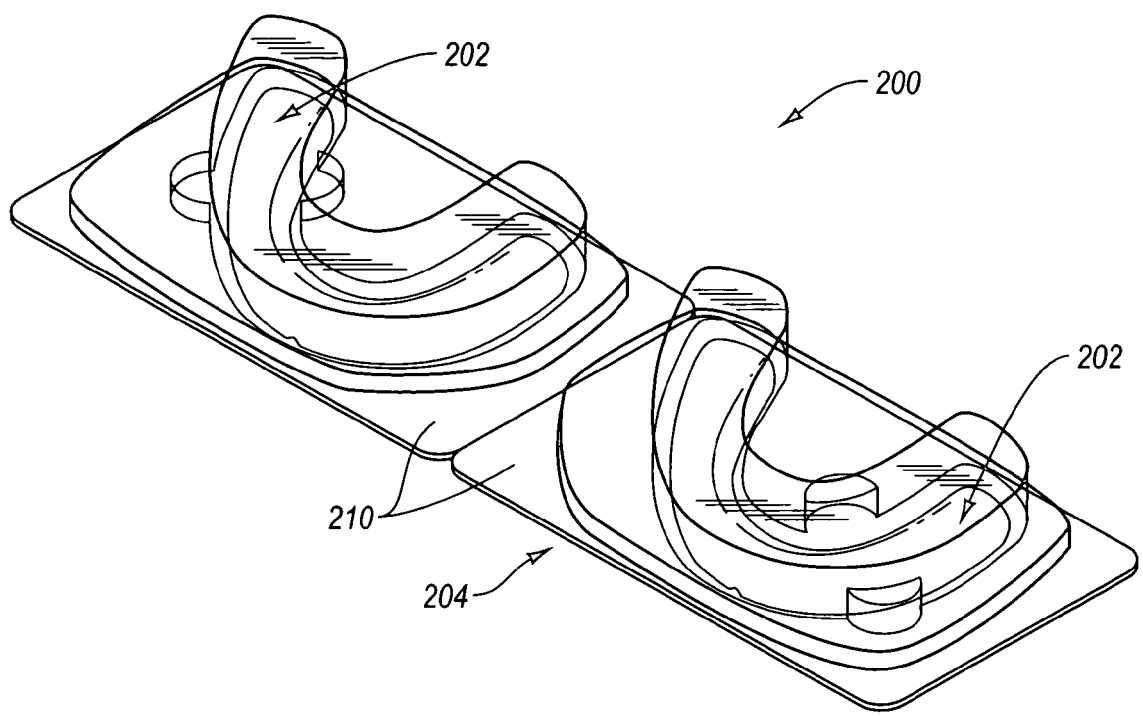

FIGS. 2A-2C illustrate another system 200. FIG. 2A illustrates a top perspective view of the system 200 including a sealed packaging container 204. FIG. 2B illustrates a top perspective view of the system 200 with the cover 212 of packaging container 204 peeled off, and FIG. 2C illustrates a bottom perspective view of the system 200. System 200 includes two dental treatment devices 202 sealed within the packaging container 204. Dental treatment devices 202 may be identical, or for example, one device 202 may be particularly configured for placement over the upper dental arch while the other dental treatment device 202 may be configured for placement over the lower dental arch.

Similar to dental treatment device 102 of FIG. 1, dental treatment device 202 includes a tray shaped barrier layer 206 having a tray body and a trough configured for placement over a person's teeth, and a dental treatment composition 208 disposed adjacent to barrier layer 206 (e.g., disposed within the trough of barrier layer 206). Additional examples of barrier layers are disclosed in U.S. Pat. No. 6,860,736, already incorporated by reference, and U.S. patent application Ser. No. 10/783,597 filed Feb. 19, 2004 and entitled UNIVERSAL TRAY DESIGN HAVING ANATOMICAL FEATURES TO ENHANCE FIT, hereby incorporated by reference with respect to its disclosure of barrier layers and dental treatment devices.

Packaging container 204 includes a support layer 210 and a peelable cover 212. At least a portion of container 204 (e.g., support layer 210 and/or cover 212) is formed of a laminated polymer material that is substantially impervious to water molecules. In one embodiment, support layer 210 is formed of a laminated polymer material that is substantially impervious to water molecules, while cover 212 is formed of a foil material that is also impervious to water molecules.

In the illustrated example, cover 212 includes a textured surface 214 around the perimeter of cover 212. Such a textured surface may be formed by stamping cover 214 when adhering the cover to rigid support layer 210. In addition, container 204 may include perforations 216 so as to allow the user to easily separate one packaged device 202 from another without opening the sealed container 204.

As illustrated, the rigid support layer 210 may be formed (e.g., by thermoforming) so as to include a well 218 for each dental treatment device 202. The wells 218 may be configured so as to allow for a headspace between the device 202 and the cover 212.

Figure 3:
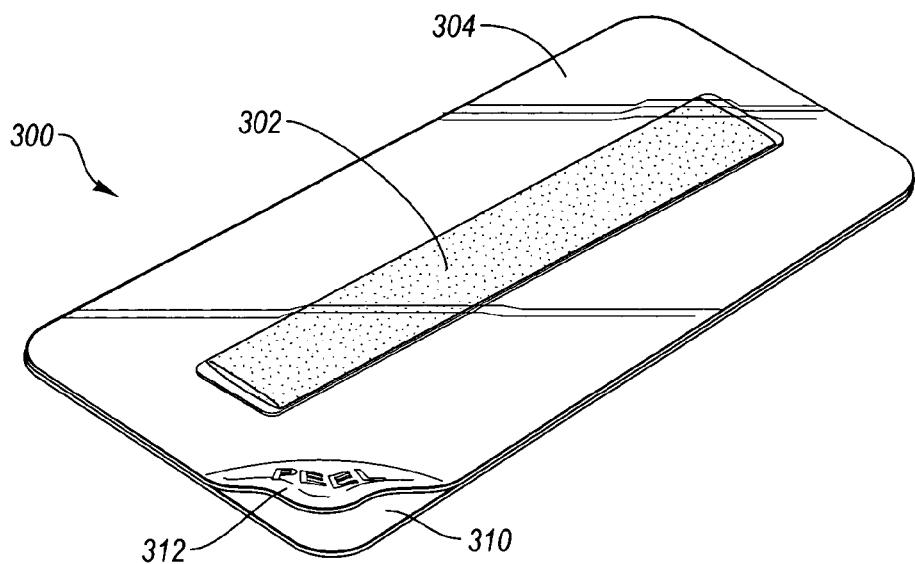
FIG. 3 illustrates another exemplary pre-packaged dental treatment system.

FIG. 3 illustrates another alternative pre-packaged dental treatment system 300 including a dental treatment device 302 sealed within a packaging container 304. Dental treatment device 302 is configured as an initially substantially flat strip that may be placed over a person's teeth, and then a portion of the strip may be folded over the occlusal surface of the covered teeth so as to effect bleaching or other treatment. Packaging container 304 includes a peelable cover 312 and a support backing layer 310. Although illustrated as transparent, cover 312 may alternatively be opaque. The peelable cover 312 and/or support layer 310 may comprise a laminated polymer material that is substantially impervious to water molecules. Although container 304 is illustrated without a head space (as opposed to the embodiments illustrated in FIGS. 1A-2C), it is to be understood that any of the embodiments may or may not include a head space between the device and the container, as desired.

The embodiments of dental treatment devices illustrated in FIGS. 1-3 are intended to be illustrative of some possible barrier layer configurations (e.g., trays and strips). It is to be understood that the dental treatment device disposed and sealed within the packaging container may include a barrier layer having any desired configuration in addition to those specifically illustrated.

Figure 4:
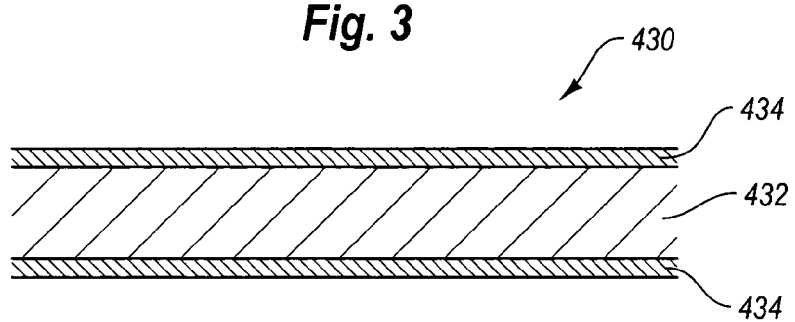
FIG. 4 illustrates a cross sectional view of a portion of an exemplary sealed packaging container.

A portion of the sealed packaging container (e.g., the support layer and/or the cover) may be formed of any suitable laminated polymer material that is substantially impervious to water molecules so as to protect the potency of a dental treatment composition contained within the container. FIG. 4 illustrates a cross sectional view of one exemplary laminated polymer material. Laminated polymer material 430 is illustrated as including a core layer 432 sandwiched between two outer layers 434. Core layer 432 may comprise a material having good water and/or oxygen molecule barrier properties (i.e., low permeability to water and/or oxygen molecules). An example of such a class of materials includes a cyclic olefin copolymer (COC) or a polychlorotrifluoroethylene (PCTFE). ACLAR, available from Honeywell Specialty Films in Morristown, N.J., is one example of a suitable PCTFE material.

Outer layers 434 may be formed of any suitable polymer material different from core layer 432, and may be selected according to any desired property (e.g., good bondability to core material 432, good $O_2$ barrier characteristics, good flow characteristics, low cost). For example, outer layers 434 may be formed of polypropylene (PP), while core 432 is formed of a COC. Polypropylene is easily bondable to COC, provides structure and bulk to the laminate polymer film, and is relatively inexpensive. Other outer layer materials may include, but are not limited to, polyethylene (PE), polyvinylchloride (PVC), polyvinyldichloride (PVDC), or a glycol-modified polyethylene terephthalate (PETG). The composite laminate material acts as a good barrier to water molecules and optionally oxygen molecules.

Figure 5:
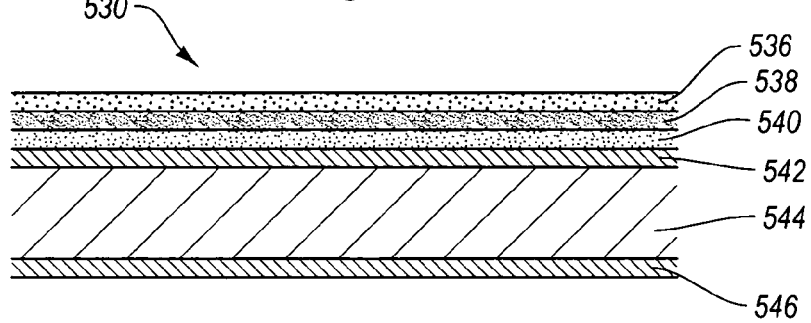
FIG. 5 illustrates a cross sectional view of a portion of another exemplary sealed packaging container.

FIG. 5 illustrates a cross section of another laminated polymer material 530. Laminate 530 is illustrated as including a total of six layers. In one example, the first three layers (536, 538, and 540) may include a layer providing laminate 530 with good $O_2$ barrier properties, while the last three layers (542, 544, 546) may include a layer providing laminate 530 with good water molecule barrier properties, such that laminate 530 acts as an effective barrier to both water molecules and $O_2$ (i.e., laminate 530 is substantially impervious to both water molecules and $O_2$). The remaining layers may be selected based on any desirable property (e.g., good bondability to an adjacent layer, good flow characteristics, or low cost). For example, layers 536 and 540 may comprise polyethylene, while layer 538 may comprise ethylvinyl hydroxide (EVOH). Layer 538 formed of EVOH provides good $O_2$ barrier properties (i.e., is substantially impervious to $O_2$) while layers 536 and 540 are formed of polyethylene so as to bond well to layer 538 and provide bulk to that portion of the laminate film. Layer 544 may be formed of a COC (selected for good water molecule barrier properties), while layers 542 and 546 may be formed of PP, selected for good bondability to COC layer 544. Polyethyelene layer 540 also exhibits good bondability to polypropylene layer 542. Although the described embodiment includes a COC layer encapsulated by PP and an EVOH layer encapsulated by PE, it is to be understood that the COC and EVOH layers may be encapsulated by any suitable materials (e.g., PP, PE, PVC, PVDC, similar materials, or combinations thereof).

The layers may be co-extruded, using the heat of the extrusion process to bond the layers together, or the layers may be bonded together by use of suitable adhesives.

Figure 6:
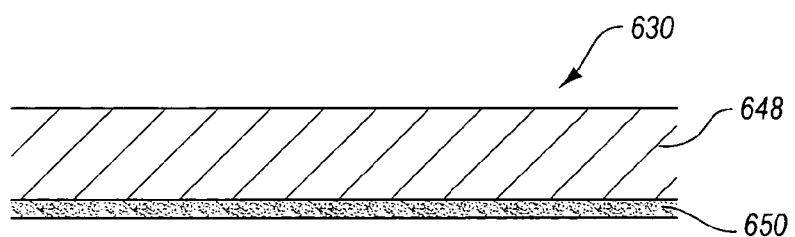
FIG. 6 illustrates a cross sectional view of a portion of another exemplary sealed packaging container.

FIG. 6 illustrates another cross section of a laminate polymer material 630 including just two layers 648 and 650. In one such embodiment, one layer (e.g., layer 648) may be formed of a material selected for its good $O_2$ barrier properties, while the other (e.g., layer 650) may be formed of a material selected for its good water molecule barrier properties. An example of such an embodiment may include a layer 648 formed of BAREX, a nitrile copolymer available from BP Chemicals Inc., located in Naperville, Ill., while layer 650 may be formed of ACLAR, a PCTFE available from Honeywell Specialty Films in Morristown, N.J.

III. Exemplary Method of Use

Figure 7A:
FIGS. 7A and 7B illustrate a person placing the dental treatment devices of FIGS. 1A-1C over both the upper and lower dental arches.
Figure 7B:
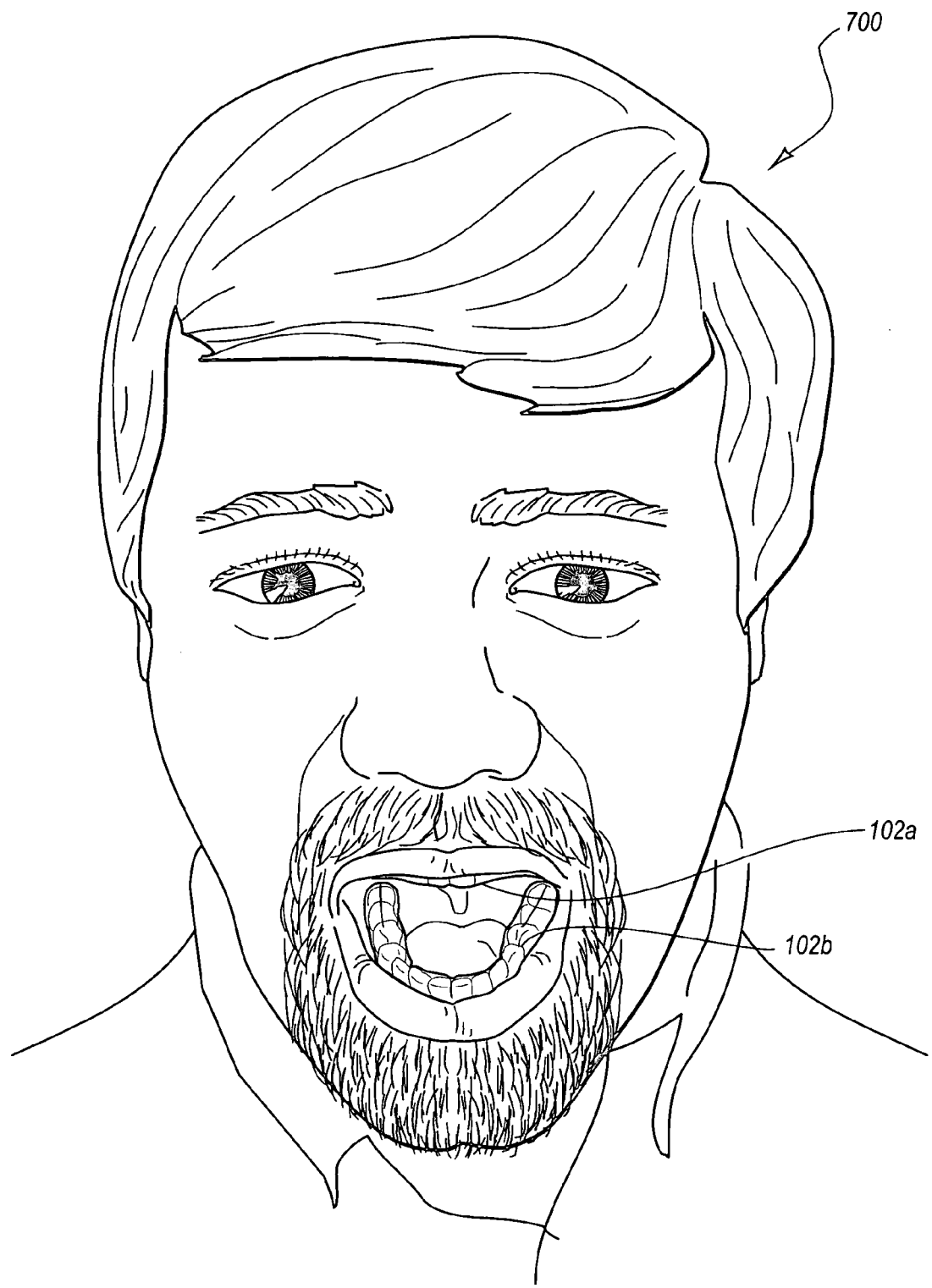

In use, the user simply opens the container and removes the dental bleaching device from the packaging container. The dental bleaching device may then be placed over the person's teeth as desired. FIG. 7A illustrates a person 700 placing a dental bleaching device 102a over the person's upper dental arch. FIG. 7B shows the person 700 with both a dental bleaching device 102a over the person's upper dental arch and a bleaching device 102b over the lower dental arch. After use, a user can pry open a corner of the barrier layer using a fingernail or rigid tool and then pull the remainder off the teeth. Any residual dental bleaching composition that remains adhered to the person's teeth can be removed by washing or flushing water over the person's teeth, and/or by brushing.

EXAMPLE 1

A laminate polymer film suitable for thermoforming a support layer for a packaging container having 6 layers and showing good $O_2$ barrier properties and being substantially impervious to water molecules is formed by co-extrusion. The layer compositions and thicknesses are initially as follows:

| | | |
|---|---|---|
| $1^{st}$ Layer | PP | 1.5 mils |
| $2^{nd}$ Layer | COC | 12 mils |
| $3^{rd}$ Layer | PP | 1.5 mils |
| $4^{th}$ Layer | PE | 1.2 mils |
| $5^{th}$ Layer | EVOH | 0.4 mil |
| $6^{th}$ Layer | PE | 1.2 mils |

A support layer having a well is thermoformed from the laminate polymer film. A dental treatment device is placed within the well, and a peelable foil cover is adhered over the support layer. The sealed packaging container acts as a substantially impervious barrier to both water molecules and $O_2$, allowing the dental treatment composition sealed within the container to exhibit good stability, even when stored at room temperature for 24 months or more.

EXAMPLE 2

A laminate polymer film suitable for thermoforming a support layer for a packaging container having 6 layers and showing good $O_2$ barrier properties and being substantially impervious to water molecules is formed by co-extrusion. The layer compositions and thicknesses are initially as follows:

| | | |
|---|---|---|
| 1st Layer | PP | 1.5 mils |
| 2nd Layer | COC | 15 mils |
| 3rd Layer | PP | 1.5 mils |
| 4th Layer | PE | 1.2 mils |
| 5th Layer | EVOH | 0.4 mil |
| 6th Layer | PE | 1.2 mils |

A support layer having a well is thermoformed from the laminate polymer film. A dental treatment device is placed within the well, and a peelable foil cover is adhered over the support layer. The sealed packaging container acts as a substantially impervious barrier to both water molecules and $O_2$, allowing the dental treatment composition sealed within the container to exhibit good stability, even when stored at room temperature for 24 months or more.

EXAMPLE 3

A laminate polymer film suitable for thermoforming a support layer for a packaging container having 6 layers and showing good $O_2$ barrier properties and being substantially impervious to water molecules is formed by co-extrusion. The layer compositions and thicknesses are initially as follows:

| | | |
|---|---|---|
| 1st Layer | PP | 1.5 mils |
| 2nd Layer | COC | 18 mils |
| 3rd Layer | PP | 1.5 mils |
| 4th Layer | PE | 1.2 mils |
| 5th Layer | EVOH | 0.4 mil |
| 6th Layer | PE | 1.2 mils |

A support layer having a well is thermoformed from the laminate polymer film. A dental treatment device is placed within the well, and a peelable foil cover is adhered over the support layer. The sealed packaging container acts as a substantially impervious barrier to both water molecules and $O_2$, allowing the dental treatment composition sealed within the container to exhibit good stability, even when stored at room temperature for 24 months or more.

EXAMPLE 4

A laminate polymer film suitable for thermoforming a support layer for a packaging container having 3 layers and being substantially impervious to water molecules is formed by co-extrusion. The layer compositions and thicknesses are initially as follows:

| | | |
|---|---|---|
| 1st Layer | PP | 1.5 mils |
| 2nd Layer | COC | 15 mils |
| 3rd Layer | PP | 1.5 mils |

A support layer having a well is thermoformed from the laminate polymer film. A dental treatment device is placed within the well, and a peelable foil cover is adhered over the support layer. The sealed packaging container acts as a substantially impervious barrier to water molecules, allowing the dental treatment composition sealed within the container to exhibit good stability, even when stored at room temperature for 24 months or more.

EXAMPLE 5

A laminate polymer film suitable for thermoforming a support layer for a packaging container having 3 layers and being substantially impervious to water molecules is formed by co-extrusion. The layer compositions and thicknesses are initially as follows:

| | | |
|---|---|---|
| 1st Layer | PP | 1.5 mils |
| 2nd Layer | COC | 18 mils |
| 3rd Layer | PP | 1.5 mils |

A support layer having a well is thermoformed from the laminate polymer film. A dental treatment device is placed within the well, and a peelable foil cover is adhered over the support layer. The sealed packaging container acts as a substantially impervious barrier to water molecules, allowing the dental treatment composition sealed within the container to exhibit good stability, even when stored at room temperature for 24 months or more.

EXAMPLE 6

A laminate polymer film suitable for thermoforming a support layer for a packaging container having 7 layers and showing good $O_2$ barrier properties and being substantially impervious to water molecules is formed by co-extrusion. The layer compositions and thicknesses are initially as follows:

| | | |
|---|---|---|
| 1st Layer | PP | 1.5 mils |
| 2nd Layer | COC | 12 mils |
| 3rd Layer | PP | 1.5 mils |
| 4th Layer | PE | 1.2 mils |
| 5th Layer | EVOH | 0.4 mil |
| 6th Layer | PE | 1.2 mils |
| 7th Layer | ACLAR | 2 mils |

A support layer having a well is thermoformed from the laminate polymer film. A dental treatment device is placed within the well, and a peelable foil cover is adhered over the support layer. The sealed packaging container acts as a substantially impervious barrier to both water molecules and $O_2$, allowing the dental treatment composition sealed within the container to exhibit good stability, even when stored at room temperature for 24 months or more.

EXAMPLE 7

A laminate polymer film suitable for thermoforming a support layer for a packaging container having 2 layers and showing good $O_2$ barrier properties and being substantially impervious to water molecules is formed by co-extrusion. The layer compositions and thicknesses are initially as follows:

| | | |
|---|---|---|
| 1st Layer | ACLAR | 3 mils |
| 2nd Layer | BAREX | 14 mils |

A support layer having a well is thermoformed from the laminate polymer film. A dental treatment device is placed within the well, and a peelable foil cover is adhered over the support layer. The sealed packaging container acts as a substantially impervious barrier to both water molecules and $O_2$, allowing the dental treatment composition sealed within the container to exhibit good stability, even when stored at room temperature for 24 months or more.

EXAMPLE 8

A laminate polymer film suitable for thermoforming a support layer for a packaging container having 3 layers and being substantially impervious to water molecules is cold formed. The layer compositions and thicknesses are initially as follows:

| | | |
|---|---|---|
| 1st Layer | PP | 1.5 mils |
| 2nd Layer | COC | 15 mils |
| 3rd Layer | PP | 1.5 mils |

A support layer having a well is thermoformed from the laminate polymer film. A dental treatment device is placed within the well, and a peelable foil cover is adhered over the support layer. The sealed packaging container acts as a substantially impervious barrier to water molecules, allowing the dental treatment composition sealed within the container to exhibit good stability, even when stored at room temperature for 24 months or more.

EXAMPLE 9

A laminate polymer film suitable for thermoforming a support layer for a packaging container having 6 layers and showing good $O_2$ barrier properties and being substantially impervious to water molecules was formed. The layer compositions and thicknesses were initially as follows:

| | | |
|---|---|---|
| 1st Layer | PP | 1.5 mils |
| 2nd Layer | COC | 12 mils |
| 3rd Layer | PP | 1.5 mils |
| 4th Layer | PE | 1.2 mils |
| 5th Layer | EVOH | 0.4 mil |
| 6th Layer | PE | 1.2 mils |

A support layer having a well was thermoformed from the laminate polymer film. A dental treatment device was placed within the well, and a peelable foil cover was adhered over the support layer. The sealed packaging container acted as a substantially impervious barrier to both water molecules and $O_2$. Even after 14 months in storage at 25° C., the dental treatment composition sealed within the container continued to exhibit good stability.

EXAMPLE 10

A laminate polymer film suitable for thermoforming a support layer for a packaging container manufactured by re-arranging the polymer layers of Examples 1-9.

EXAMPLE 11

A laminate polymer film suitable for cold forming a support layer for a packaging container manufactured by substituting a polymer layer of Examples 1-10 with a metal foil layer.

It will be appreciated that the present claimed invention may be embodied in other specific forms without departing from its spirit or essential characteristics. The described embodiments are to be considered in all respects only as illustrative, not restrictive. The scope of the invention is, therefore, indicated by the appended claims rather than by the foregoing description. All changes that come within the meaning and range of equivalency of the claims are to be embraced within their scope.

The invention claimed is:

1. A pre-packaged dental treatment system comprising:
 a dental treatment device comprised of;
  a barrier layer configured for placement over at least a portion of a person's teeth; and
  a dental treatment composition disposed adjacent to the barrier layer; and
 a sealed packaging container within which the dental treatment device is disposed, at least a portion of which comprises a laminated polymer material having a first laminate portion that is substantially impervious to water molecules selected from the group consisting of cyclic olefin copolymer and polychlorotrifluoroethylene, and a second laminate portion that is substantially impervious to oxygen molecules selected from the group consisting of an ethylvinyl hydroxide and a nitrile copolymer.

2. A pre-packaged dental treatment system as recited in claim 1, wherein the laminated polymer material further comprises at least one material selected from the group consisting of polypropylene, polyethylene, polyvinyl chloride, polyvinyldichloride, and glycol-modified polyethylene terephthalate.

3. A pre-packaged dental treatment system as recited in claim 1, wherein the laminated polymer material has a thickness between about 6 and about 30 mils.

4. A pre-packaged dental treatment system as recited in claim 1, wherein the laminated polymer material has a thickness between about 12 and about 28 mils.

5. A pre-packaged dental treatment system as recited in claim 1, wherein the laminated polymer material has a thickness between about 15 and about 25 mils.

6. A pre-packaged dental treatment system as recited in claim 1, wherein the laminated polymer material comprises a core sandwiched between two outer layers.

7. A pre-packaged dental treatment system as recited in claim 1, wherein the sealed packaging container further includes a cover comprising foil, paper, a laminate, or a combination thereof.

8. A pre-packaged dental treatment system as recited in claim 1, wherein the laminated polymer material is transparent.

9. A pre-packaged dental treatment system as recited in claim 1, wherein the barrier layer comprises a tray having a tray body and a trough.

10. A pre-packaged dental treatment system as recited in claim 1, wherein the barrier layer comprises a strip that is initially substantially flat.

11. A pre-packaged dental treatment system as recited in claim 1, further comprising a head space between the dental treatment device and at least a portion of the sealed packaging container.

12. A pre-packaged dental treatment system as recited in claim 1, wherein the dental treatment composition comprises at least one of a desensitizing agent, a remineralizing agent, an antimicrobial agent, an anti-plaque agent, an anti-tartar agent, a gingival soothing agent, an anesthetic, an anti-oxidant, or a mouth freshening agent.

13. A pre-packaged dental treatment system as recited in claim 1, wherein the dental treatment composition comprises a dental bleaching agent.

14. A pre-packaged dental treatment system as recited in claim 13, wherein the dental bleaching agent comprises at least one material selected from the group consisting of aqueous hydrogen peroxide, carbamide peroxide, a metal perborate, a metal percarbonate, a metal peroxide, a metal chlorite or hypochlorite, a peroxy acid, and a peroxy acid salt.

15. A pre-packaged dental treatment system as recited in claim 1, the dental treatment composition further comprising at least one thickening agent selected from the group consisting of polyvinyl pyrrolidone (PVP), a PVP-vinyl acetate copolymer, carboxypolymethylene, polyethylene oxide, polyacrylic acid, a polyacrylic acid polymer or copolymers, a polyacrylate, a polyacrylamide, a copolymer of polyacrylic acid and polyacrylamide, carboxymethylcellulose, carboxypropylcellulose, a cellulosic ether, a polysaccharide gum, and a protein.

16. A pre-packaged dental treatment system comprising:
    a dental treatment device comprising;
        a barrier layer configured for placement over at least a portion of a person's teeth; and
        a dental treatment composition disposed adjacent to the barrier layer; and
    a sealed packaging container within which the dental treatment device is disposed, the sealed packaging container comprising a core cyclic olefin copolymer sandwiched between outer layers of polypropylene, the sealed packaging container being substantially impervious to water molecules.

17. A pre-packaged dental treatment system comprising:
    a dental treatment device comprising;
        a barrier layer configured for placement over at least a portion of a person's teeth; and
        a dental treatment composition disposed adjacent to the barrier layer; and
    a sealed packaging container within which the dental treatment device is disposed, at least a portion of which comprises a laminated polymer material having a first laminate portion that is substantially impervious to water molecules, and a second laminate portion that is of a material different than the first laminate portion and is substantially impervious to oxygen molecules.

* * * * *

UNITED STATES PATENT AND TRADEMARK OFFICE
CERTIFICATE OF CORRECTION

PATENT NO. : 7,568,579 B2　　　　　　　　　　　　　　　　　　　　　　Page 1 of 1
APPLICATION NO. : 11/284472
DATED : August 4, 2009
INVENTOR(S) : Moore It is certified that error appears in the above-identified patent and that said Letters Patent is hereby corrected as shown below:

Column 1
Line 64, change "available practical." to --available or practical.--

Column 2
Line 67, change "full" to --fully--

Signed and Sealed this

First Day of December, 2009

David J. Kappos
*Director of the United States Patent and Trademark Office*

UNITED STATES PATENT AND TRADEMARK OFFICE
CERTIFICATE OF CORRECTION

PATENT NO.       : 7,568,579 B2                                  Page 1 of 1
APPLICATION NO.  : 11/284472
DATED            : August 4, 2009
INVENTOR(S)      : Scott Eric Moore It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 923 days.

Signed and Sealed this

Seventh Day of September, 2010

David J. Kappos
*Director of the United States Patent and Trademark Office*